United States Patent [19]

Iwamatsu et al.

[11] 4,357,331
[45] Nov. 2, 1982

[54] 7αMETHOXYCEPHALOSPORIN DERIVATIVES

[75] Inventors: Katsuyoshi Iwamatsu; Shigeharu Inoue; Keinosuke Miyauchi; Shinichi Kondo, all of Yokohama; Shigeo Seki, Tokyo; Yujiro Yamada, Yokohama, all of Japan

[73] Assignee: Meiji Seika Kaisha, Ltd., Tokyo, Japan

[21] Appl. No.: 104,220

[22] Filed: Dec. 17, 1979

[30] Foreign Application Priority Data

Dec. 18, 1978 [JP] Japan ................. 53-154997

[51] Int. Cl.³ ................. C07D 501/36; A61K 31/545
[52] U.S. Cl. ....................... 424/246; 544/21; 544/26
[58] Field of Search ............. 544/27, 28, 21, 26, 544/30; 424/246

[56] References Cited

U.S. PATENT DOCUMENTS

| 4,007,177 | 2/1977 | Nakao et al. | 544/21 |
| 4,051,129 | 9/1977 | Shimizu et al. | 544/21 |
| 4,059,578 | 11/1977 | DeMarinis et al. | 544/21 |
| 4,126,745 | 11/1978 | Nakao et al. | 544/21 |
| 4,165,429 | 8/1979 | Iwanami et al. | 544/21 |
| 4,297,488 | 10/1981 | Christensen et al. | 544/21 |

Primary Examiner—Nicholas S. Rizzo
Attorney, Agent, or Firm—Sughrue, Mion, Zinn, Macpeak & Seas

[57] ABSTRACT

A 7α-methoxycephalosporin derivative represented by the formula (I):

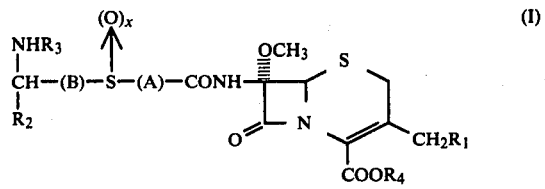

wherein $R_1$ represents a heterocyclic ring or an —S— heterocyclic ring; $R_2$ represents a hydrogen atom, a carboxy group or a —COOR$_5$ group wherein $R_5$ represents a lower alkyl group, a dialkylamino-lower alkyl group or a

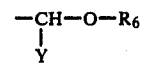

group wherein $R_6$ represents a lower alkyl group, a lower acyl group or a lower alkoxycarbonyl group and Y represents a hydrogen atom or a lower alkyl group; $R_3$ represents a hydrogen atom, a carbamoyl group or a lower acyl group; $R_4$ represents a hydrogen atom, a lower alkyl group, a dialkylamino-lower alkyl group or a

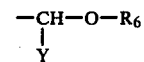

group wherein $R_6$ and Y are defined as above; A and B, which may be the same or different, each represents a straight chain or branched chain alkylene group having 1 to 5 carbon atoms; and x represents 0 or 1; or a pharmaceutically acceptable salt thereof and a process for producing the same.

7 Claims, No Drawings

7α-METHOXYCEPHALOSPORIN DERIVATIVES

BACKGROUND OF THE INVENTION

1. Field of the Invention

This invention relates to a 7α-methoxycephalosporin derivative, a pharmaceutically acceptable salt thereof and a process for producing the same. The 7α-methoxycephalosporin derivative or salt thereof according to this invention is a novel compound which possesses high antibacterial activity.

2. Description of the Prior Art

Cephalosporin type compounds have antibacterial activity and many derivatives of them have been produced to date. Some of the derivatives (e.g., cephalexin and cephalotin) are used therapeutically as excellent antibacterial agents. As a result of recent studies on a cephamycin type compound which has a methoxy group at 7α-position of the cephalosporin ring (e.g., cefoxitin), many derivatives that belong to this type have been reported. However, very few conventional cephalosporin type compounds exhibit satisfactory antibacterial activity against both gram-positive and gram-negative bacteria.

SUMMARY OF THE INVENTION

As a result of various studies that aim at locating a 7α-methoxycephalosporin derivative having high antibacterial activity, it has been found that a novel compound of the following formula (I) exhibits high antibacterial activity that cannot be supplied by any of the conventional 7α-methoxycephalosporin derivatives.

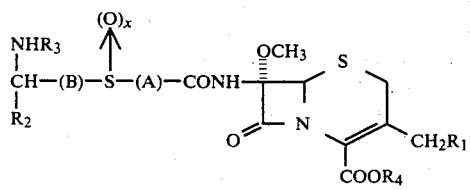

wherein $R_1$ represents a heterocyclic ring or an —S-heterocyclic ring; $R_2$ represents a hydrogen atom, a carboxy group (i.e., —COOH group) or a —COOR$_5$ group wherein $R_5$ represents a lower alkyl group, a dialkylamino-lower alkyl group or a

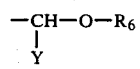

group wherein $R_6$ represents a lower alkyl group, a lower acyl group or a lower alkoxycarbonyl group and Y represents a hydrogen atom or a lower alkyl group; $R_3$ represents a hydrogen atom, a carbamoyl group (i.e., —CONH$_2$ group) or a lower acyl group; $R_4$ represents a hydrogen atom, a lower alkyl group, a dialkylamino-lower alkyl group or a

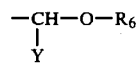

group wherein $R_6$ and Y are as defined above; A and B, which may be the same or different, each represents a straight chain or branched chain alkylene group having 1 to 5 carbon atoms; and x represents 0 or 1; or a pharmaceutically acceptable salt thereof.

DETAILED DESCRIPTION OF THE INVENTION

The compound of the formula (I) according to this invention can exist in the form of an inner salt when $R_2$, $R_3$ and $R_4$ of the formula are each a hydrogen atom, and in other cases, the compound can advantageously exist in the form of a pharmaceutically acceptable salt thereof. If $R_2$ is a carboxyl group or a —COOR$_5$ group, the compound can take the form of either D-stereoisomer or L-stereoisomer, both of which are included within the scope of this invention. The D-form usually has a higher bacterial activity than the L-form except that $R_3$ is an acyl group substituted with an amino group.

The heterocyclic ring of $R_1$ is a 5- or 6-membered heterocyclic ring containing 1 to 4 nitrogen atoms as the hetero atom. The heterocyclic ring may further contain 1 or 2 sulfur atoms as the hetero atom other than the nitrogen atom. A preferred heterocyclic ring is a 5- or 6-membered heterocyclic ring containing 1 to 4 nitrogen atoms as the hetero atom.

The lower acyl group of $R_3$ is a straight or branched chain aliphatic acyl group containing 1 to 6 carbon atoms which may be substituted with a halogen atom or an amino group. Preferred acyl group of $R_3$ is a straight or branched chain aliphatic acyl group containing 1 to 4 carbon atoms, such as a formyl group, an acetyl group, a trifluoroacetyl group, a glycyl group, an alanyl group and a propionyl group.

The lower alkyl group of $R_4$ and $R_5$ is a straight or branched chain alkyl group having 1 to 6 carbon atoms, preferably 1 to 4 carbon atoms.

In the dialkylamino-lower alkyl group of $R_4$ and $R_5$, each alkyl moiety is a straight or branched chain alkyl moiety having 1 to 6 carbon atoms, preferably 1 to 4 carbon atoms.

The alower alkyl group of $R_6$ is a straight or branched chain alkyl group having 1 to 6 carbon atoms, preferably 1 to 4 carbon atoms.

The acyl group of $R_6$ is an unsubstituted straight or branched chain aliphatic acyl group having 1 to 6 carbon atoms.

In the alkoxycarbonyl group of $R_6$, the alkyl moiety is a straight or branched chain alkyl moiety having 1 to 6 carbon atoms, preferably 1 to 4 carbon atoms.

The lower alkyl group of Y is a straight or branched chain alkyl group having 1 to 4 carbon atoms.

The alkylene group of A and B is a straight or branched chain alkylene group having 1 to 5 carbon atoms, preferably 1 to 3 carbon atoms.

The x is preferably 0.

More specifically, the 7α-methoxycephalosporin derivative of the present invention is represented by the following formulae (I-a), (I-b) or (I-c):

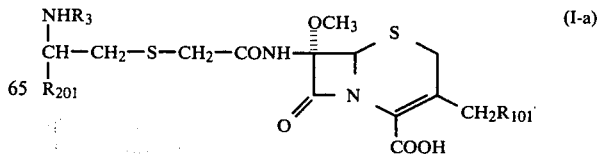

wherein R$_{101}$ represents ,

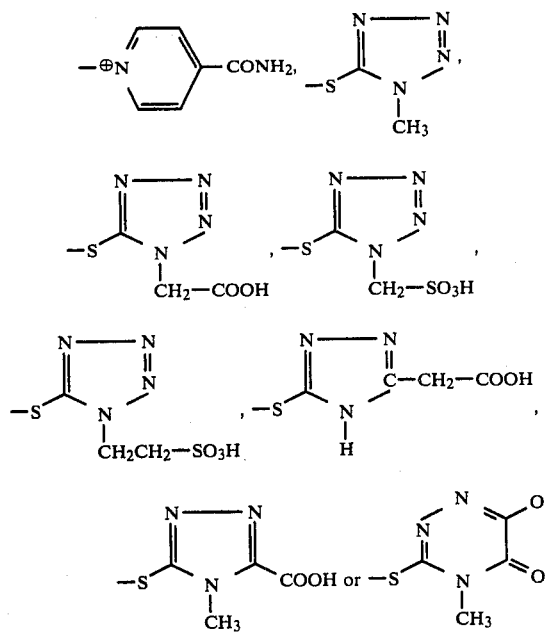

R$_{201}$ represents a hydrogen atom or a carboxy group; R$_3$ represents a hydrogen atom, a carbamoyl group or a lower acyl group;

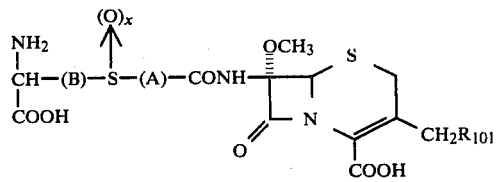 (I-b)

wherein R$_{101}$ is the same as defined in the formula (I-a); A and B, which may be the same or different, each represents a straight chain or branched chain alkylene group having 1 to 5 carbon atoms; x represents 0 or 1;

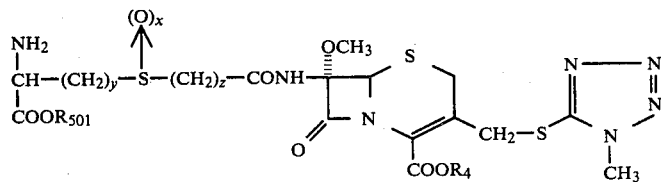

wherein R$_4$ and R$_{501}$, which may be the same or different, each represents a hydrogen atom, a lower alkyl group, a dialkylamino-lower alkyl group or

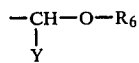

wherein R$_6$ represents a lower alkyl group, a lower acyl group or a lower alkoxycarbonyl group and Y represents a hydrogen atom or a lower alkyl group; x is 0 or 1; y and z, which may be the same or different, each represents an integer of 1 to 5; provided that both R$_4$ and R$_{501}$ are not a hydrogen atom; or pharmaceutically acceptable salts thereof.

In the formula (I-a), R$_3$ represents a hydrogen atom, a carbamoyl group or a lower acyl group. The lower acyl group of R$_3$ is a straight or branched chain aliphatic acyl group containing 1 to 6 carbon atoms which may be substituted with a halogen atom or an amino group. Preferred lower acyl groups include a formyl group, an acetyl group, a trifluoroacetyl group, a propionyl group, a glycyl group and an alanyl group. Illustrative 3-positioned substituents containing heterocyclic rings are 5-(1-methyl-1H-tetrazolyl)thiomethyl, 5-(1-carboxymethyl-1H-tetrazolyl)thiomethyl, 5-(1-sulfomethyl(or sulfoethyl)-1H-tetrazolyl)thiomethyl, and 5-(2-carboxymethyl-1H-triazolyl)thiomethyl, 5-(2-carboxymethyl-1-methyl-1H-triazolyl)thiomethyl, 3-(4-methyl-5-oxo-6-hydroxy-4,5-dihydro-1,2,4-triazinyl)-thiomethyl, pyridiniummethyl and p-carbamoylpyridiniummethyl.

Illustrative compounds of the formula (I-a) according to this invention include the following:

7β-aminoethylthioacetamido-7α-methoxy-3-(1-methyl-1H-tetrazol-5-yl)thiomethyl-3-cephem-4-carboxylic acid, 7β-ureidoethylthioacetamido-7α-methoxy-3-(1-methyl-1H-tetrazol-5-yl)thiomethyl-3-cephem-4-carboxylic acid, 7β-(2D-2-amino-2-carboxy)ethylthioacetamido-7α-methoxy-3-(1-methyl-1H-tetrazol-5-yl)thiomethyl-3-cephem-4-carboxylic acid, 7β-(2DL-2-amino-2-carboxy)ethylthioacetamido-7α-methoxy-3-(1-methyl-1H-tetrazol-5-yl)thiomethyl-3-cephem-4-carboxylic acid, 7β-(2L-2-amino-2-carboxy)ethylthioacetamido-7α-methoxy-3-(1-methyl-1H-tetrazol-5-yl)thiomethyl-3-cephem-4-carboxylic acid, 7β-aminoethylthioacetamido-7α-methoxy-3-(1-carboxymethyl-1H-tetrazol-5-yl)thiomethyl-3-cephem-4-carboxylic acid, 7β-ureidoethylthioacetamido-7α-methoxy-3-(1-carboxymethyl-1H-tetrazol-5-yl)thiomethyl-3-cephem-4-carboxylic acid, 7β-(2D-2-amino-2-carboxy)ethylthioacetamido-7α-methoxy-3-(1-carboxymethyl-1H-tetrazol-5-yl)thiomethyl-3-cephem-4-carboxylic acid, 7β-aminoethylthioacetamido-7α-methoxy-3-(1-sulfomethyl-1H-tetrazol-5-yl)thiomethyl-3-cephem-4-

(I-c)

carboxylic acid,

7β-aminoethylthioacetamido-7α-methoxy-3-(1-sulfoethyl-1H-tetrazol-5-yl)thiomethyl-3-cephem-4-carboxylic acid, 7β-ureidoethylthioacetamido-7α-methoxy-3-(1-sulfomethyl-1H-tetrazol-5-yl)thiomethyl-3-cephem-4-carboxylic acid, 7β-(2D-2-amino-2-carboxy)ethylthioacetamido-7α-methoxy-3-(1-sulfomethyl-1H-tetrazol-5-yl)thiomethyl-3-cephem-4-carboxylic acid 7β-(2D-2-amino-2-carboxy)ethylthioacetamido-7α-methoxy-3-(1-sulfoethyl-1H-tetrazol-5-yl)thiomethyl-3-cephem-4-carboxylic acid, 7β-trifluoroacetamidoethylthioacetamido-7α-methoxy-3-(1-methyl-1H-tetrazol-5-yl)thiomethyl-3-cephem-4-carboxylic acid, 7β-formamidoethylthioacetamido-7α-methoxy-3-(1-methyl-1H-tetrazol-5-yl)thiomethyl-3-cephem-4-carboxylic acid, 7β-acetamidoethylthioacetamido-7α-methoxy-3-(1-methyl-1H-tetrazol-5-yl)thiomethyl-3-cephem-4-carboxylic acid, 7β-aminoethylthioacetamido-7α-methoxy-3-(2-carboxymethyl-1H-triazol-5-yl)thiomethyl-3-cephem-4-carboxylic acid, 7β-D-alanylaminoethylthioacetamido-7α-methoxy-3-(1-methyl-1H-tetrazol-5-yl)thiomethyl-3-cephem-4-carboxylic acid, 7β-(2L-2-ureido-2-carboxy)ethylthioacetamido-7α-methoxy-3-(1-methyl-1H-tetrazol-5-yl)thiomethyl-3-cepehm-4-carboxylic acid, 7β-aminoethylthioacetamido-7α-methoxy-3-(p-carboxyamidopyridinium)methyl-3-cephem-4-carboxylic acid, 7β-(2D-2-amino-2-carboxy)ethylthioacetamido-7α-methoxy-3-(p-carboxyamidopyridinium)methyl-3-cephem-4-carboxylic acid, 7β-(2D-2-amino-2-carboxy)ethylthioacetamido-7α-methoxy-3-pyridiniummethyl-3-cephem-4-carboxylic acid, 7β-(2D-2-amino-2-carboxy)ethylthioacetamido-7α-methoxy-3-(2-carboxymethyl-1-methyl-1H-triazol-5-yl)thiomethyl-3-cephem-4-carboxylic acid, and 7β-(2D-2-amino-2-carboxy)ethylthioacetamido-7α-methoxy-3-(4-methyl-5-oxo-6-hydroxy-4,5-dihydro-1,2,4-triazin-3-yl)thiomethyl-3-cephem-4-carboxylic acid.

In the formula (I-b) examples of the 3-positioned substituent including a heterocyclic ring are the same ones as for the formula (I-a) above.

Illustrative compounds of the formula (I-b) of this invention include the following:

7β-(3D-3-amino-3-carboxy)propylthioacetamido-7α-methoxy-3-(1-methyl-1H-tetrazol-5-yl)thiomethyl-3-cephem-4-carboxylic acid, 7β-(3D-3-amino-3-carboxy)propylsulfinylacetamido-7α-methoxy-3-(1-methyl-1H-tetrazol-5-yl)thiomethyl-3-cephem-4-carboxylic acid, 7β-(3D-3-amino-3-carboxy)propylthioacetamido-7α-methoxy-3-(2-carboxymethyl-1H-triazol-5-yl)thiomethyl-3-cephem-4-carboxylic acid, 7β-(3D-3-amino-3-carboxy)propylthioacetamido-7α-methoxy-3-(p-carbamoyl-pyridinium)methyl-3-cephem-4-carboxylic acid, 7β-(3DL-3-amino-3-carboxy)propylthioacetamido-7α-methoxy-3-(1-methyl-1H-tetrazol-5-yl)thiomethyl-3-cephem-4-carboxylic acid, 7β-(2D-2-amino-2-carboxy)ethylthiopropionamido-7α-methoxy-3-(1-methyl-1H-tetrazol-5-yl)thiomethyl-3-cephem-4-carboxylic acid, 7β-(3D-3-amino-3-carboxy)propylthiopropionamido-7α-methoxy-3-(1-methyl-1H-tetrazol-5-yl)thiomethyl-3-cephem-4-carboxylic acid, 7β-(4D-4-amino-4-carboxybutylthioacetamido)-7α-methoxy-3-(1-methyl-1H-tetrazol-5-yl)thiomethyl-3-cephem-4-carboxylic acid, and 7β-(2D-2-amino-2-carboxy-1,1-dimethyl)ethylthioacetamido-7α-methoxy-3-(1-methyl-1H-tetrazol-5-yl)thiomethyl-3-cephem-4-carboxylic acid.

Examples of the pharmaceutically acceptable salts of the compound of the formulae (I-a) and (I-b) are alkali metal salts such as sodium salt and basic amino acid salts such as L-lysine salt. The terminal amino acid at 7-position of the formulae (I-a), (I-b) and (I-c) may assume either D-stereoisomer or L-stereoisomer, and both types are included within the scope of this invention. The D-form usually has a higher bacterial activity than the L-form except that $R_3$ is an acy group substituted with an amino group.

The 7α-methoxycephalosporin derivative of the formula (I-c) exhibits high antibacterial activity through oral or parenteral administration, especially through oral administration.

The compound of the formula (I-c) of this invention may be used in the form of a free base when two carboxylic groups are esterified but it is more advantageously used in the form of a pharmaceutically acceptable acid addition salt with, for example, hydrochloric acid, sulfuric acid, phosphoric acid, acetic acid, tartaric acid, maleic acid, succinic acid, glutamic acid or aspartic acid or inner salt. These acid addition salts or inner salt are not only highly stable but they are also highly soluble in water and therefore are convenient for administration. In addition, their ability to form a uniform dispersion results in increased therapeutic effect.

Referring now to the formula (I-c), $R_4$ and $R_{501}$ each represents a hydrogen atom, a lower alkyl group (such as methyl, ethyl, propyl or t-butyl) and dimethylaminoethyl, methoxymethyl, ethoxymethyl, 1-ethoxyethyl ($-CH_2(CH_3)-OEt$), acetoxymethyl, 1-acetoxyethyl, propionyloxymethyl, 1-propionyloxyethyl, pivaloyloxymethyl, 1-pivaloyloxyethyl, methoxycarbonyloxymethyl, 1-methoxycarbonyloxyethyl, ethoxycarbonyloxymethyl, 1-ethoxycarbonyloxyethyl, etc.

The terminal amino acid at the 7-positioned substituent can assume either D- or L-stereoisomer, and D- or L-stereoisomer and their racemic form are included within the scope of this invention. The D-form usually exhibits higher in vivo antibacterial activity than the L-form.

Illustrative compounds of the formula (I-c) of this invention are listed below:

7β-(2D-2-amino-2-methoxycarbonyl)ethylthioacetamido-7α-methoxy-3-(1-methyl-1H-tetrazol-5-yl)thiomethyl-3-cephem-4-carboxylic acid, 7β-(2D-2-amino-2-ethoxycarbonyl)ethylthioacetamido-7α-methoxy-3-(1-methyl-1H-tetrazol-5-yl)thiomethyl-3-cephem-4-carboxylic acid, 7β-(2D,L-2-amino-2-ethoxycarbonyl)ethylthioacetamido-7α-methoxy-3-(1-methyl-1H-tetrazol-5-yl)thiomethyl-3-cephem-4-carboxylic acid, 7β-(3D-3-amino-3-ethoxycarbonyl)propylthioacetamido-7α-methoxy-3-(1-methyl-1H-tetrazol-5-yl)thiomethyl-3-cephem-4-carboxylic acid, Methoxymethyl 7β-(2D-2-amino-2-methoxycarbonyl)ethylthioacetamido-7α-methoxy-3-(1-methyl-1H-tetrazol-5-yl)thiomethyl-3-cephem-4-carboxylate, Methoxymethyl 7β-(3D-3-amino-3-ethoxycarbonyl)propylthioacetamido-7α-methoxy-3-(1-methyl-1H-tetrazol-5-yl)thiomethyl-3-cephem-4-carboxylate, 1-Ethoxyethyl 7β-(2D-2-amino-2-ethoxycarbonyl)ethylthiopropionamido-7α-methoxy-3-(1-methyl-1H-tetrazol-5-yl)thiomethyl-3-cephem-4-carboxylate,
1-Ethoxyethyl 7β-(2D-2-amino-2-ethoxycarbonyl)ethylthioacetamido-7α-methoxy-3-(1-methyl-1H-tetrazol-5-yl)thiomethyl-3-cephem-4-carboxylate,
Dimethylaminoethyl 7β-(2D-2-amino-2-methoxycarbonyl)ethylthioacetamido-7α-methoxy-3-(1-methyl-1H-tetrazol-5-yl)thiomethyl-3-cephem-4-carboxylate,
Dimethylaminoethyl 7β-(2D-2-amino-2-ethoxycarbonyl)ethylthioacetamido-7α-methoxy-3-(1-methyl-1H-tetrazol-5-yl)thiomethyl-3-cephem-4-carboxylate,
1-Acetoxyethyl 7β-(2D-2-amino-2-carboxy)ethylthioacetamido-7α-methoxy-3-(1-methyl-1H-tetrazol-5-yl)thiomethyl-3-cephem-4-carboxylate,
Acetoxymethyl 7β-(2D-2-amino-2-methoxycarbonyl)ethylthioacetamido-7α-methoxy-3-(1-methyl-1H-tetrazol-5-yl)thiomethyl-3-cephem-4-carboxylate,
1-Acetoxyethyl 7β-(2D-2-amino-2-ethoxycarbonyl)ethylthioacetamido-7α-methoxy-3-(1-methyl-1H-tetrazol-5-yl)thiomethyl-3-cephem-4-carboxylate,
1-Acetoxyethyl 7β-(2D-2-amino-ethoxycarbonyl)ethylsulfoxideacetamido-7α-methoxy-3-(1-methyl-1H-tetrazol-5-yl)thiomethyl-3-cephem-4-carboxylate,
1-Acetoxyethyl 7β-(3D-3-amino-ethoxycarbonyl)propylthioacetamido-7α-methoxy-3-(1-methyl-1H-tetrazol-5-yl)thiomethyl-3-cephem-4-carboxylate,
Pivaloyloxymethyl 7β-(2D-2-amino-2-methoxycarbonyl)ethylthioacetamido-7α-methoxy-3-(1-methyl-1H-tetrazol-5-yl)thiomethyl-3-cephem-4-carboxylate,
1-Pivaloyloxyethyl 7β-(2D-2-amino-2-ethoxycarbonyl)ethylthioacetamido-7α-methoxy-3-(1-methyl-1H-tetrazol-5-yl)thiomethyl-3-cephem-4-carboxylate,
Methoxycarbonyloxymethyl 7β-(2D-2-amino-2-methoxycarbonyl)ethylthioacetamido-7α-methoxy-3-(1-methyl-1H-tetrazol-5-yl)thiomethyl-3-cephem-4-carboxylate,
1-Ethoxycarbonyloxyethyl 7β-(2D-2-amino-2-ethoxycarbonyl)ethylthioacetamido-7α-methoxy-3-(1-methyl-1H-tetrazol-5-yl)methylthio-3-cephem-4-carboxylate,
1-Acetoxyethyl 7β-(2D-2-amino-2-acetoxyethoxycarbonyl)ethylthioacetamido-7α-methoxy-3-(1-methyl-1H-tetrazol-5-yl)thiomethyl-3-cephem-4-carboxylate,
1-Pivaloyloxyethyl 7β-(2D-2-amino-2-pivaloyloxyethoxycarbonyl)ethylthioacetamido-7α-methoxy-3-(1-methyl-1H-tetrazol-5-yl)thiomethyl-3-cephem-4-carboxylate, and
Methoxymethyl 7β-(2D-2-amino-2-methoxymethoxycarbonyl)ethylthioacetamido-7α-methoxy-3-(1-methyl-1H-tetrazol-5-yl)thiomethyl-3-cephem-4-carboxylate.

The compounds of the formulae (I-a) and (I-b) exhibit high antibacterial activity against a wide spectrum of pathogenic bacteria. The compounds of the formulae (I-a) and (I-b) exhibit antibacterial activity not only in vitro but also in vivo. The activity of the compounds of this invention against several species of bacteria is shown in the following Table 1 from which one can see the effectiveness of the compounds as compared with the control cefoxitin (manufactured by Merck Co.).

TABLE 1

| Microorganism | MIC* (mcg/ml) | | | | | | |
|---|---|---|---|---|---|---|---|
| | Compound of Ex. 1 | Compound of Ex. 2 | Compound of Ex. 3 | Compound of Ex. 11 | Compound of Ex. 12 | Compound of Ex. 13 | Cefoxitin |
| Staphylococcus aureus 209p | 1.56 | 3.13 | 6.25 | 3.13 | 6.25 | 12.5 | 1.56 |
| Bacillus anthracis No. 119 | 0.39 | 0.78 | 0.78 | 0.20 | 1.56 | 1.56 | 3.13 |
| Escherichia coli 255 | 6.25 | 12.5 | 12.5 | 0.78 | 3.13 | 3.13 | 50 |
| Citrobacter freundii | 1.56 | 25 | 25 | 25 | 25 | 50 | 50 |
| Klebsiella pneumoniae | 3.13 | 1.56 | 0.78 | 1.56 | 6.25 | 6.25 | 3.13 |
| Proteus morganii | 6.25 | 3.13 | 0.39 | 3.13 | 12.5 | 12.5 | 6.25 |
| Serratia marcescens No. 1 | 3.13 | 3.13 | 1.56 | 0.78 | 12.5 | 25 | 3.13 |
| Pseudomonas aeruginosa IFO 3080 | 25 | 25 | 50 | 100 | 6.25 | 100 | 100 |

*The bacteria were pre-incubated in tripticase soy broth (manufactured by BBL) at 37° C. for overnight and then diluted to 100-fold with the same broth as used above to provide inoculum. A nutrient agar (Difco) as a medium for measurement of MIC was inoculated with the resulting inoculum and incubated at 37° C. for 20 hours to determine MIC (minimum inhibitory concentration).

The compounds of the formula (I-c) exhibit only weak antibacterial activity in vitro, but when they are administered in vivo, the ester linkage easily breaks to let them exhibit a strong antibacterial activity. The in vivo antibacterial activity ($ED_{50}$) of several compounds of this invention as administered to mice orally is tabulated in Table 2 from which one can see the effectiveness of the compounds as compared with the controls cephalexin and cefoxitin.

TABLE 2

| | Route of Administration | $ED_{50}$ (mg/mouse)* with Escherichia coli No. 29 |
|---|---|---|
| Compound of Example 17 | oral | 0.86 |
| | subcutaneous | 0.046 |
| Compound of Example 18 | oral | 0.36 |
| | subcutaneous | 0.24 |
| Compound of Example 19 | oral | 0.25 |
| | subcutaneous | 0.17 |
| Cephalexin | oral | 1.60 |
| | subcutaneous | — |
| Cefoxitin | oral | >5.0 |
| | subcutaneous | 0.43 |

*Male ddY mice (5 mice per group, each weighing 20 g on average) were challenged intraperitoneally with a suspension of 7.9 × 10⁴ (31.9 $LD_{50}$) cells of preincubated Escherichia coli No. 29 in 2.5% aqueous mucin. Immediately after the inoculation, the test compounds and controls dissolved or suspended in 0.2 ml of physiological saline were administered to the mice, which were fed for a week to observe the fatality. The $ED_{50}$ values were calculated by the Probit method.

The substances of the general formula (I) of the present invention show an $LD_{50}$ value of about 6 to 8 g/kg upon intravenous injection in mice and are substantially non-toxic.

It is therefore concluded that the compound of the formula (I) of the present invention is advantageously used as a medicine for treating bacterially caused diseases. For this purpose, the compound of the formulae (I-a) and (I-b) may be administered either parenterally in the form of intravenous or muscular injection or a suppository or orally in the form of a tablet, powder, capsule, syrup, etc., and the compound of the formula (I-c) may preferably be administered orally in the form of a tablet, powder, capsule, syrup, etc. If an addition salt of the compound (I-c) is water-soluble, it may be administered parenterally in the form of intravenous or muscular injection or a suppository.

It will be appreciated that the actual preferred dosage of the active substance of this invention used will vary according to the particular composition formulated for administration, the mode of administration and the particular disease to be treated. Many factors that modify the action of the drug of this invention will be taken into account by the skilled in the art, for example, age, body weight, sex, diet, time of administration, route of administration, rate of excretion, drug combinations, reaction sensitivities and severity of the disease. Generally, in case of intravenous or intramuscular administration of the compound of the formulae (I-a) and (I-b), 1 g of the active compound is given a day to an adult person and, when a patient has a severe disease 2 to 4 g of the active compound is given a day to an adult person. In case of oral administration of the compound of the formula (I-c), 0.5 to 1 g of the active compound is given a day to an adult person.

The 7α-methoxycephalosporin derivative represented by the formula (I) can be prepared by (i) reacting a compound of the formula (II):

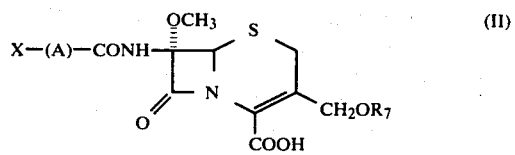

wherein X represents a halogen atom (for example, chlorine, bromine and iodine atom), $R_7$ represents an acetyl group, a carbamoyl group, an α-methoxy-p-sulfoxycinnamoyl group or a p-hydroxycinnamoyl group and A represents a straight or branched chain alkylene group having 1 to 5 carbon atoms; with a compound of the formula (III):

wherein $R_{201}$ represents a hydrogen atom or a carboxy group, $R_3$ represents a hydrogen atom, a carbamoyl group or a lower acyl group, and B represents a straight or branched chain alkylene group having 1 to 5 carbon atoms, using an inert solvent (for example, water, methanol and aqueous acetone) in the presence of a base as an acid scavenger (for example, an alkali metal hydrogencarbonate, trialkylamine, and pyridine) at room temperature or lower for about 1 to 5 hours to produce a compound of the formula (IV):

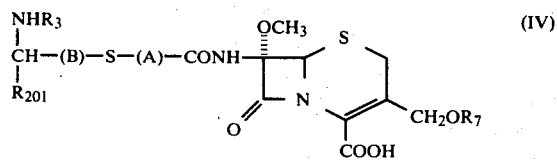

wherein $R_{201}$, $R_3$, $R_7$, A and B are as defined above, and further reacting the compound of the formula (IV) with a nucleophilic reagent (e.g., pyridine, p-carbamoylpyridine, 5-mercapto-1-methyl-1H-tetrazole, 5-mercapto-1H-tetrazole-1-acetic acid, 5-mercapto-1H-tetrazole-1-methanesulfonic acid, 5-mercapto-1H-tetrazole-1-ethanesulfonic acid, 5-mercapto-1H-triazole-2-acetic acid, 5-mercapto-1H-triazole-2-carboxylic acid, 3-mercapto-4-methyl-5-oxo-6-hydroxy-4,5-dihydro-1,2,4-triazine), using a solvent (for example, water) under substantially neutral condition (for example, pH of 6.0-7.5) at 40° to 70° C. for 7 to 20 hours; (ii) reacting a compound of the formula (VI):

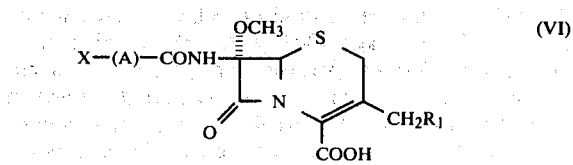

wherein $R_1$ represents a heterocyclic ring or an —S—heterocyclic ring, A represents a straight or branched chain alkylene group having 1 to 5 carbon atoms and X represents a halogen atom, with a compound of the formula (III):

wherein B, $R_3$ and $R_{201}$ have the same meaning as defined above, using a solvent (for example, water, methanol, aqueous acetone) in the presence of an acid scavenger (for example, an alkali metal hydrogencarbonate, trialkylamine and pyridine) under substantially neutral condition (such as pH of 6.5-7.5) at room temperature or lower for about 30 minutes to 5 hours; or (iii) reacting a compound of the formula (VII):

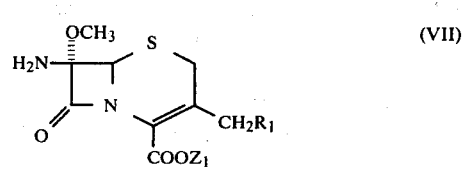

wherein $R_1$ represents a heterocyclic ring or an —S—heterocyclic ring and $Z_1$ represents a removable carboxyl-protecting group with a compound of the formula (VIII):

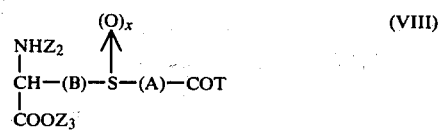

wherein A and B, which may be the same or different, each represents a straight or branched chain alkylene group having 1 to 5 carbon atoms, $Z_2$ represents a removable amino-protecting group, $Z_3$ represents a removable carboxyl-protecting group, x is 0 or 1 and T is a hydroxyl group or an atom or group necessary to form an active derivative of carboxylic acid such as an acid halide, a mixed acid anhydride, succinimide and p-nitrophenyl ester. The reaction is conducted using a solvent (for example, dichloromethane chloroform, benzene and dimethylformamide) in the presence of an acid scavenger (for example, trialkylamine, pyridine and N,N-dimethylaniline) or a dehydrative-condensation agent (for example, N,N'-dicyclohexylcarbodiimide) at room temperature or lower for 1 to 5 hours, and further removing the protecting groups $Z_1$, $Z_2$ and $Z_3$, if necessary.

In the above preparation method, the starting compound of the formula (II) can be obtained in a conventional manner, for example, the method described in *Chemical and Pharmaceutical Bulletin,* Vol. 24, page 2629 (1976) and the method described in *Tetrahedron Letters,* No. 16, page 1307 (1976); the starting compound of the formula (VI) can be obtained in a conventional manner, for example, the method described in U.S. Pat. No. 4,115,645; and the starting compound of the formula (VII) can be obtained in a conventional manner, for example, the method described in *Journal of Antibiotics,* Vol. 29, page 554 (1976), the method described in *Tetrahedron Letters,* page 2705 (1975) or the method described in *J. Am. Chem. Soc.,* Vol. 99, page 5504 (1977).

The preparation of the compound of the formula (I) of the present invention is described hereinafter in more detail.

The compound of the formula (I-a) of this invention can be prepared by reacting a compound of the formula (II-a):

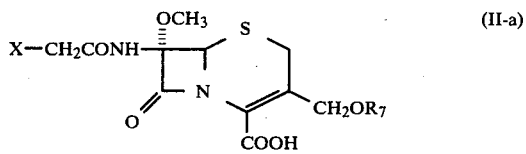

wherein X represents a halogen atom, and $R_7$ represents an acetyl group, a carbamoyl group, an α-methoxy-p-sulfoxycinnamoyl group or a p-hydroxycinnamoyl group; with a compound of the formula (III-a):

wherein $R_{201}$ represents a hydrogen atom or a carboxy group and $R_3$ represents a hydrogen atom, a carbamoyl group or a lower acyl group; to produce a compound of the formula (IV-a):

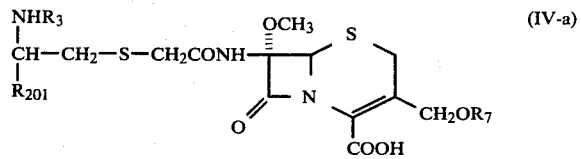

wherein $R_{201}$, $R_7$ and $R_3$ have the same meaning as defined above; and further reacting the compound of the formula (IV-a) with a nucleophilic reagent (e.g., pyridine, p-carbamoylpyridine, 5-mercapto-1-methyl-1H-tetrazole, 5-mercapto-1H-tetrazole-1-acetic acid, 5-mercapto-1H-tetrazole-1-methanesulfonic acid, 5-mercapto-1H-tetrazole-1-ethanesulfonic acid, 5-mercapto-1H-triazole-2-acetic acid, 5-mercapto-1H-triazole-2-carboxylic acid, 3-mercapto-4-methyl-5-oxo-6-hydroxy-4,5-dihydro-1,2,4-triazine) or an alkali metal salt thereof.

The compound of the formula (II-a) used as a starting material can be obtained in a conventional manner, for example, by the method described in *Chemical and Pharmaceutical Bulletin,* Vol. 24, page 2629 (1976) and *Tetrahedron Letters,* No. 16, page 1307 (1976).

Of the halogen atoms for X in the formula (II-a), i.e., chlorine, bromine and iodine; bromine is preferred.

The reaction for producing the compound of the formula (IV-a) from the compound of the formula (II-a) and the compound of the formula (III-a) is generally carried out using a suitable inert solvent in the presence of an acid scavenger in a molar ratio of about 1 to 1.5 to the reactants. Any solvent may be used in this reaction without particular limitation so long as it does not enter the reaction, and suitable examples of the solvent are water and methanol. Examples of the acid scavenger are such bases as an alkali metal hydrogencarbonate, trialkylamine and pyridine. The compound (II-a) reacts with the compound (III-a) in the presence of such acid scavenger at room temperature or lower to form the compound (IV-a). The reaction time depends mainly on the type of halogen, acid scavenger and solvent, and it generally ranges from 1 hour to 5 hours.

The compound of the formula (IV-a) thus prepared may be recovered from the reaction mixture by a conventional method, if necessary. For example, the reaction mixture is diluted with water, adsorbed on an adsorptive resin (e.g., Diaion HP-20, etc.) or activated carbon and eluted with a water-containing organic solvent for purification purpose. If necessary, the compound may be subjected to column chromatography on various types of adsorbents (e.g., Diaion HP-20, etc.) for further purification. The compound of the formula (IV-a) thus obtained is 7β-[2-amino(or carbamoylated or acylated amino)ethylthioacetamido]-7α-methoxy-3-acetoxymethyl-3- cephem-4-carboxylic acid and 7β-[2-amino(or carbamoylated or acylated amino)-2-carboxyethylthioacetamido]-7α-methoxy-3-acetoxymethyl-3-cephem-4-carboxylic acid.

The resulting compound of the formula (IV-a) is further reacted with a nucleophilic reagent (e.g., pyridine, p-carbamoylpyridine, 5-mercapto-1-methyl-1H-tetrazole, 5-mercapto-1H-tetrazole-1-acetic acid, 5-mercapto-1H-tetrazole-1-methanesulfonic acid, 5-mercapto-1H-tetrazole-1-ethanesulfonic acid, 5-mercapto-1H-triazole-2-acetic acid, 5-mercapto-1H-triazole-2-carboxylic acid, 3-mercapto-4-methyl-5-oxo-6-hydroxy-4,5-dihydro-1,2,4-triazine) or an alkali metal salt thereof such as sodium salt or potassium salt using a solvent. Any solvent may be used without particular limitation so long as it does not enter the reaction, and water is preferred. The reaction is preferably carried out under substantially neutral condition pH 6.0–7.5, and if the nucleophilic reagent described above is very slightly soluble in water, the reaction is desirably carried out in an aqueous solution in the presence of a base such as an alkali hydroxide or alkali phosphate so as to convert the compound into a salt of such base. There is no particular limitation on the reaction temperature, but a temperature of about 40° to 70° C. is used to advantage. The substitution reaction described above takes somewhat longer than the reaction for producing a cephalosporin having no 7α-methoxy, and it usually takes about 7 to 20 hours when the reaction temperature is 70° C.

According to a modified process for producing the compound (I-a) of this invention, a compound of the formula (III-a):

wherein $R_{201}$ represents a hydrogen atom or a carboxy group and $R_3$ represents a hydrogen atom, a carbamoyl group or a lower acyl group or a salt thereof is reacted with a compound of the formula (VI-a):

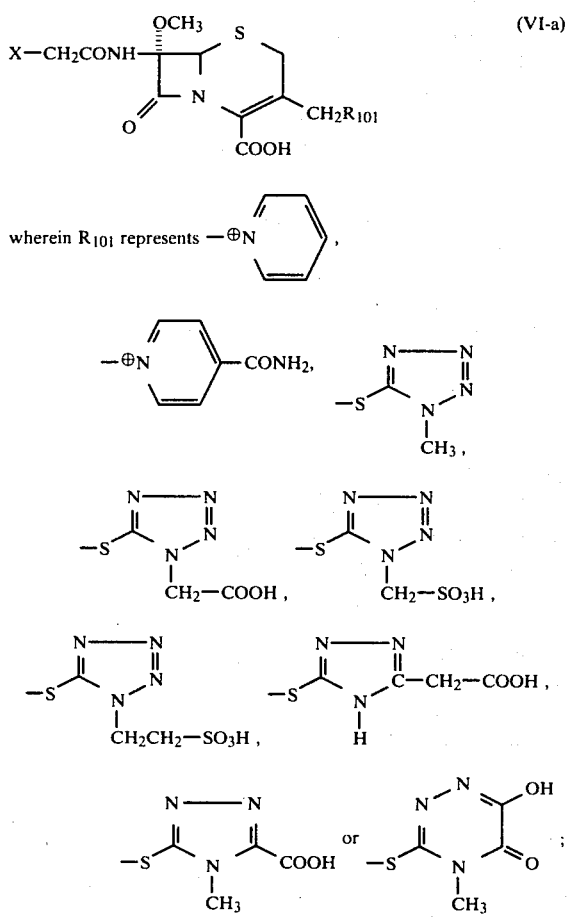

and X represents a halogen atom or a salt thereof.

The compound of the formula (VI-a) is obtained by a conventional method, for example, the method described in U.S. Pat. No. 4,115,645.

The halogen atom X in the formula (VI-a) is chlorine, bromine or iodine, and chlorine and bromine are preferred.

The reaction for producing a compound of the formula (I-a) from the compound (VI-a) is generally carried out having the compound of the formula (III-a) act on the compound (VI-a) in an inert solvent in the presence of an acid scavenger. Any solvent may be used in this reaction without particular limitation so long as it does not enter the reaction, and suitable examples are water, methanol and acetone. Examples of the acid scavenger are such bases such as an alkali metal hydrogen-carbonate, trialkylamine and pyridine. The compound (VI-a) reacts with the compound (III-a) in the presence of such acid scavenger at room temperature or lower under about neutral pH (pH 6.5 to 7.5) to form the compound of the formula (I-a). The reaction time depends mainly on the activity of halogen, type of acid scavenger and solvent, and it generally ranges from about 30 minutes to 5 hours.

The reaction product may be recovered from the reaction mixture in a conventional manner. For instance, the reaction mixture is rendered acidic to cause precipitation of the reaction product which is then recovered. Alternatively, the reaction product is adsorbed on activated carbon or adsorptive resin (e.g., Diaion HP-20), eluted with a water-containing solvent and subjected to column chromatography on Sephadex LH-20 or G-10 (manufactured by Pharmacia, Sweden) for purification purpose.

A compound of the formula (I-a) wherein $R_3$ is a carbamoyl or acyl group may also be obtained by reacting a compound of the formula (I-a) obtained by the method described above (wherein $R_3$ is a hydrogen atom) with a carbamoylation reagent such as an alkali metal cyanate or carbamoyl chloride or an acylation reagent such as S-ethyltrifluorothioacetate, trifluoroacetic anhydride, formic acid-carbonic acid anhydride, or acetic anhydride. The reaction may be carried out in a solvent that does not enter the reaction (e.g., water, pyridine, or dimethylformamide), and is completed in several hours (5 to 30 hours) at room temperature or lower under neutral to weak alkaline condition (pH 7.5–8). After the reaction, the end compound of the formula (I-a) wherein $R_3$ is a carbamoyl or acyl group may be conveniently purified and recovered by adsorption on activated carbon or adsorptive resin, elution, and column chromatography on Sephadex LH-20 or G-10.

The compound of the formula (I-b) of this invention can be prepared by reacting a compound of the formula (III-1):

wherein B is a straight chained or branched alkylene group having 1 to 5 carbon atoms, or a salt thereof, with a compound of the formula (VI-b):

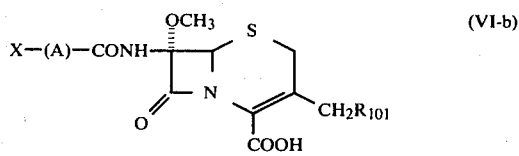

wherein A is a straight chained or branched alkylene group having 1 to 5 carbon atoms; $R_{101}$ is the same as defined in the formula (I-a); X is a halogen atom or a salt thereof. The compound of the formula (VI-b) is obtained by a conventional method, for example, the method described in U.S. Pat. No. 4,115,645.

The halogen atom X in the formula (VI-b) is chlorine, bromine or iodine, and chlorine and bromine are preferred.

The reaction for producing a compound of the formula (I-b) from the compound (VI-b) is generally carried out by having the compound of the formula (III-1) act on the compound (VI-b) in an inert solvent in the presence of an acid scavenger. Any solvent may be used in this reaction without particular limitation so long as it does not enter the reaction, and suitable examples are water, methanol and acetone. Examples of the acid scavenger are such bases as an alkali metal hydrogencarbonate, trialkylamine and pyridine. The compound (VI-b) reacts with the compounds (III-1) in the presence of such acid scavenger at room temperature or lower under about neutral pH (pH 6.5–7.5) to form the compound of the formula (I-b). The reaction time depends mainly on the activity of halogen, and the type of acid scavenger and solvent, and it generally ranges from 30 minutes to 5 hours.

According to a modified process for producing the compound (I-b) of this invention, a compound of the formula (VII-b):

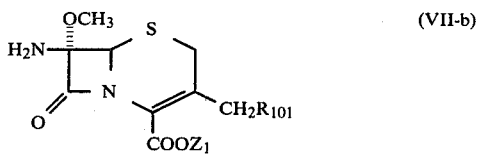

wherein $R_{101}$ is as defined above, and $Z_1$ is a removable carboxy-protecting group, is reacted with a compound of the formula (VIII):

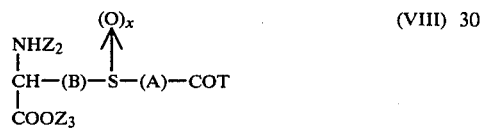

wherein $Z_2$ is a removable amino-protecting group; $Z_3$ is a removable carboxyl-protecting group; A and B are each a straight chained or branched alkylene group having 1 to 5 carbon atoms; x is 0 or 1; T is a hydroxyl group or an atom or group necessary to form an active derivative of carboxylic acid (such as an acid halide, a mixed anhydride, succinimide and p-nitrophenyl ester), with $Z_1$, $Z_2$ and $Z_3$ optionally removed from the reaction product.

The compound of the formula (VII-b) used as a starting material is obtained in a conventional manner, for example, by the method described in *Journal of Antibiotics*, Vol. 29, page 554 (1976), the method described in *Tetrahedron Letters*, page 2705 (1975) or the method described in *J. Am. Chem. Soc.*, Vol. 99, page 5504 (1977). The compound of the formula (VIII) is obtained by reacting a compound of the formula (IX):

wherein $Z_2$, $Z_3$ and B are the same as defined above, with a compound of the formula (X):

wherein X is a halogen atom, and A is a straight chained or branched alkylene group having 1 to 5 carbon atoms, optionally followed by having a sulfoxide forming agent such as hydrogen peroxide act on the reaction product, and further followed by having an acid halide forming agent such as thionyl chloride or a mixed acid anhydride forming agent such as ethyl chlorocarbonate act on the product.

$Z_2$ of the formula (IX) is an amino-protecting group such as t-butoxycarbonyl or trichloroethoxycarbonyl group; $Z_3$ of the formula (IX) and $Z_1$ of the formula (VII-b) are a carboxyl-protecting group such as a diphenyl methyl or trichloroethyl group, and are introduced or removed by a conventional method. Referring to the formula (X), the halogen atom is chlorine, bromine or iodine, and bromine is preferred.

According to this invention, the compound of the formula (I-b) is produced from the compound of the formula (VII-b), and the reaction for producing the compound (I-b) can generally be carried out by having the compound (VIII) act on the compound (VII-b) in an inert solvent under conditions that form an amide linkage. Any solvent may be used in this reaction without particular limitation so long as it does not enter the reaction. Illustrative suitable solvents are organic solvents such as dichloromethane, chloroform, benzene and dimethylformamide. When the compound of the formula (VIII) is an acid halide, the compounds (VII-b) and (VIII) react with each other in the presence of an acid scavenger, e.g., a base such as trialkylamine, N,N-dimethylaniline, or pyridine, at room temperature or lower. Removal of the amino- and carboxyl-protecting groups gives the compound of the formula (I-b). The reaction time varies primarily with the activity of the carboxylic acid derivative and it generally ranges from 1 to 5 hours.

If T of the formula (VIII) is a hydroxyl group, the compound (I-b) can be obtained by reacting the compound (VIII) with the compound (VII-b) in the presence of a dehydration-condensation agent such as N,N'-dicyclohexylcarbodiimide.

The compound of the formula (I-b) thus prepared may be recovered from the reaction mixture by a conventional method. For instance, the reaction mixture is diluted with water, adsorbed on an adsorptive resin or activated carbon, and eluted with a water-containing organic solvent for purification purpose. If necessary, further purification and isolation may be achieved by column chromatography on Sephadex LH-20 or G-10 (manufactured by Pharmacia, Sweden) or Diaion HP-20 (manufactured by Mitsubishi Chemical Industries Limited).

The compound of the formula (I-c) of this invention can be prepared by reacting a compound of the formula (XI):

wherein $R_6$ is a lower alkyl group, a lower acyl group or a lower alkoxycarbonyl group; Y is a hydrogen atom or a lower alkyl group; X is a halogen atom, with any of the novel compounds of the formula (I'):

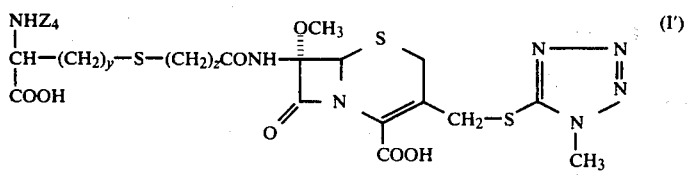

(I')

wherein $Z_4$ is a hydrogen atom or a removable amino-protecting group; y and z are each an integer of 1 to 5, synthesized as above.

The halogen atom of the formula (XI) may be chlorine, bromine or iodine when $R_6$ is a lower alkyl or a lower alkoxycarbonyl group, i.e., alkoxyalkyl halide or alkoxycarbonyloxyalkyl halide, but only iodine is selected if $R_6$ is a lower acyl group, i.e., acyloxyalkyl halide. Illustrative removable amino-protecting groups are t-butoxycarbonyl group, adamantyloxycarbonyl group, p-nitrobenzyloxycarbonyl group, benzhydryloxycarbonyl group and 2,2,2-trichloroethoxycarbonyl group.

The esterification reaction of this invention is generally carried out by having a compound of the formula (XI) act on a compound of the formula (I') in a suitable inert solvent in the presence of a base as an acid scavenger in a molar ratio of about 1 to 1.5 to the reactants.

Any solvent may be used in this reaction without particular limitation so long as it does not enter the reaction, and suitable examples are N,N-dimethylformamide, acetonitrile, acetone, N,N-dimethylacetamide, dichloromethane, liquid sulfur dioxide, dioxane, and tetrahydrofuran. Examples of the acid scavenger are organic amines such as trialkylamine, pyridine, N-ethylaniline, dicyclohexylamine, morpholine, and N-methylmorpholine, as well as inorganic bases such as sodium hydrogencarbonate, potassium hydrogencarbonate and lithium carbonate. In the presence of such acid scavenger, and with acyloxyalkyl halide or alkoxycarbonyloxyalkyl halide used as the esterifying agent, the reaction easily proceeds at $-30°$ C. to $15°$ C., and if alkoxyalkyl halide which generally has high activity is used, the reaction proceeds easily at $-50°$ C. to $10°$ C. The reaction time depends primarily on the type of halogen, acid scavenger and solvent, and it generally ranges from 1 to 5 hours.

The compound of the formula (I-c) can also be prepared by reacting a compound of the formula (VI'):

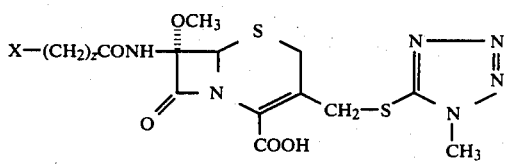

(VI')

wherein X is a halogen atom and z is an integer of 1 to 5, with a compound of the formula (XI):

(XI)

to produce a compound of the formula (XII):

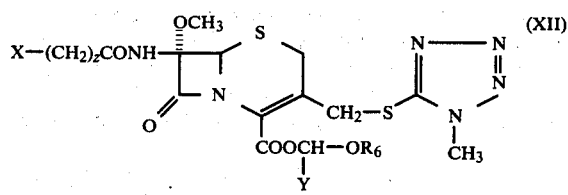

(XII)

wherein X, z, Y and $R_6$ are as defined above, and further reacting the resulting compound of the formula (XII) with a compound of the formula (III'):

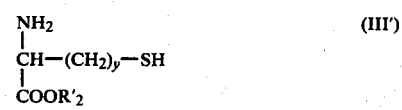

(III')

wherein $R_2'$ is a hydrogen atom or a lower alkyl group and y is an integer of 1 to 5.

The compound of the formula (VI') is obtained in a conventional method, for example, the method described in U.S. Pat. No. 4,007,177.

The reaction between the compound (VI') and the compound (XI) to form the ester of the formula (XII) is carried out under entirely the same conditions as those for the reaction between the compound (I') and the compound (XI).

The resulting compound (XII) is then reacted with cysteine or its homologue or a lower alkyl ester thereof in a solvent to produce the compound of the formula (I-c). Any solvent may be used in this reaction without particular limitation so long as it does not enter the reaction. Suitable solvents include water, methanol, ethanol, acetone, dioxane, tetrahydrofuran, and N,N-dimethylformamide, which may be used independently or as a mixture. The reaction is preferably carried out under substantially neutral conditions, and an acid or alkali may optionally be added to hold the pH of the reaction mixture between 6.5 and 7.5. The reaction proceeds at a temperature in the range of from $-10°$ C. to room temperature. The reaction time varies with the activity of halogen and the type of solvent, and generally ranges from 30 minutes to 5 hours.

A modification of the process described above comprises having a reagent of the formula (XI) act on a compound of the formula (I''):

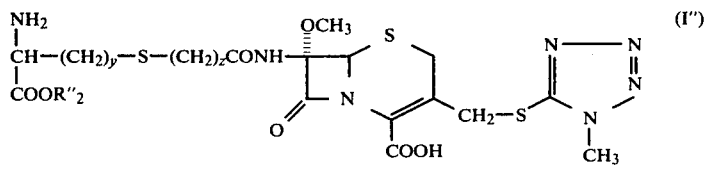

wherein $R_2''$ is a lower alkyl group; y and z each is an integer of 1 to 5, that is obtained by reacting the compound of the formula (VI′) with the compound (III′). The reaction may be carried out under conditions entirely the same as set forth above.

A dialkylamino lower alkyl ester derivative of the formula (I-c) can be easily prepared by reacting a reactive ester derivative of the N-t-butoxycarbonyl compound of the formula (I′) or (I″), (e.g., an active ester formed by using a mixed acid anhydride, p-nitrophenyl ester and carbodiimide or carbonyldiimidazole), with an N,N-dialkylamino lower alkyl alcohol in an organic solvent (such as dichloromethane, chloroform, tetrahydrofuran, N,N-dimethylformamide or dioxane), followed by using trifluoroacetic acid to remove the t-butoxycarbonyl group from the reaction product.

The compound of the formula (I-c) can also be prepared by reacting a compound of the following formula:

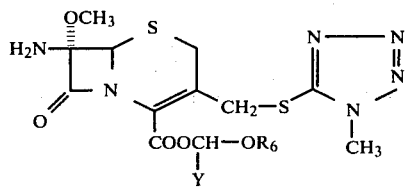

wherein $R_6$ and Y have the same meaning as defined in the formula (I-c), with a compound of the formula (VIII′):

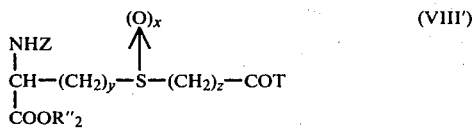

wherein $R_2''$ is a lower alkyl group; x, y and z have the same meaning as defined in the formula (I-c); Z is a hydrogen atom or a removable amino-protecting group; T is a hydroxyl group or an atom or group of atoms that form an active derivative of carboxylic acid, followed by removing the amino-protecting group from the reaction product. Examples of the amino-protecting group are those which have been mentioned in connection with the definition of the formula (I′).

Illustrative active derivatives of carboxylic acids are those which are usually employed in the formation of an amide linkage, for example, an acid halogenide such as acid chloride or acid bromide, a mixed acid anhydride such as ethoxycarbonyloxylated compound, succinimide, and p-nitrophenyl ester.

The reaction being discussed uses a dehydration-condensation agent such as dicyclohexylcarbodiimide if T of the formula (VIII′) is a hydroxyl group. Any solvent that does not enter the reaction may be used, and preferred solvents are dichloromethane, chloroform, tetrahydrofuran, dioxane, diethyl ether, and N,N-dimethylformamide. The reaction proceeds at room temperature or lower. The reaction time varies with the activity of the carboxylic acid derivative, the type of solvent and temperature, and it generally ranges from 1 to 10 hours. The ease of reaction for removing the amino-protecting group depends on the type of the protecting group, and it generally proceeds with ease in the presence of trifluoroacetic acid, zinc/acetic acid or formic acid, or by catalytic reduction.

After the reaction, the reaction product, or the end compound of the formula (I) may be effectively purified and recovered by extraction with weak alkaline solvent or acidic water extraction if the compound is a diester, and by extraction with alcohol, acetone, etc., if the compound is a monoester. If necessary, further purification may be performed by chromatography on Sephadex LH-20, etc., in a manner already described.

This invention is now described in greater detail by reference to the following examples which are given here for illustrative porposes only and are by no means intended to limit the scope of the invention.

EXAMPLE 1

1 g of 7β-bromoacetamido-7α-methoxycephalosporanic acid was suspended in 20 ml of water, $NaHCO_3$ was added to adjust the pH of the suspension to 7.0 to form an aqueous solution of the acid. Thereafter, 300 mg of mercaptoethylamine hydrochloride was added to the solution, and the reaction was carried out at room temperature for a period of 2 hours with the pH held at 7.0. After the reaction, the reaction mixture was diluted 3-fold with water, passed through a column packed with 500 ml of Diaion HP-20 (the trade name for the high porous polymer manufactured by Mitsubishi Chemical Industries Limited), washed with water, and eluted with 10% aqueous acetone. Fractions containing the end compound were concentrated, and freeze-dried to give 620 mg of 7β-aminoethylthioacetamido-7α-methoxycephalosporanic acid. 500 mg of the product was dissolved in 10 ml of water, and 155 mg of 5-mercapto-1-methyl-1H-tetrazole was added to the solution, which was then adjusted to a pH between 6.5 and 7.0 and subjected to reaction at 60° C. for a period of 7 hours. After the reaction, the reaction mixture was diluted 3-fold with water, the pH was adjusted to 6.5, passed through a column of Diaion HP-20, and eluted with 10% aqueous acetone. Fractions containing the end compound were concentrated and freeze-dried to give 250 mg of 7β-aminoethylthioacetamido-7α-methoxy-3-(1-methyl-1H-tetrazol-5-yl)thiomethyl-3-cephem-4-carboxylic acid.

Rf value in thin-layer chromatography on silica gel: 0.49 (n-butanol/acetic acid/water=2:1:1)

PMR (in heavy water, ppm values from TMS as external standard) 5.16 (1H, s), 4.16 (2H, q), 4.05 (3H, s), 3.6 (2H, q), 3.55 (3H, s), 3.5 (2H, q), 3,3 (2H, t), 3.0 (2H, t).

EXAMPLE 2

50 mg of 7β-aminoethylthioacetamido-7α-methoxy-3-(1-methyl-1H-tetrazol-5-yl)thiomethyl-3-cephem-4-carboxylic acid obtained in Example 1 was dissolved in 3 ml of water, 30 mg of potassium cyanate was added to the solution, which was then adjusted to a pH between 7.5 and 8.0 and subjected to reaction at room temperature for a period of 6 hours. After the reaction, 7 ml of water was added to the reaction mixture, the pH was adjusted to 6.5, and the mixture was passed through a column of Diaion HP-20, fractions eluted with water and containing the end compound were concentrated and freeze-dried to give 20 mg of 7β-ureidoethylthioacetamido-7α-methoxy-3-(1-methyl-1H-tetrazol-5-yl)thiomethyl-3-cephem-4-carboxylic acid.

Rf value in thin-layer chromatography on silica gel: 0.73 (n-butanol/acetic acid/water=2:1:1)

EXAMPLE 3

7β-Bromoacetamido-7α-methoxycephalosporanic acid (425 mg) was suspended in 10 ml of water, the suspension was adjusted to a pH of 7.0 to form an aqueous solution of the acid, 200 mg of D-cysteine hydrochloride was added to the solution which was then adjusted to a pH of 7.0 and subjected to reaction at room temperature for a period of 2 hours. After the reaction, the reaction mixture was treated in the same manner as in Example 1 to give 270 mg of 7β-(2-amino-2-carboxy)ethylthioacetamido-7α-methoxycephalosporanic acid. 210 mg of the product was reacted with 5-mercapto-1-methyl-1H-tetrazole, and treated with column chromatography on Diaion HP-20 to give 120 mg of the end compound, 7β-(2D-2-amino-2-carboxy)ethylthioacetamido-7α-methoxy-3-(1-methyl-1H-tetrazol-5-yl)thiomethyl-3-cephem-4-carboxylic acid.

Rf value in thin-layer chromatography on silica gel: 0.41 (n-butanol/acetic acid/water=2:1:1)

EXAMPLE 4

7β-Bromoacetamido-7α-methoxy-3-(1-methyl-1H-tetrazol-5-yl)thiomethyl-3-cephem-4-carboxylic acid (9.2 g) was suspended in 100 ml of water, and saturated aqueous sodium bicarbonate was added to the suspension under cooling to adjust its pH to 7.2 to thereby form an aqueous solution of the acid. To the solution, 4.63 g of D-cysteine hydrochloride was added under cooling, followed by stirring at room temperature for a period of from 30 to 40 minutes during which the pH was adjusted to a level between 7.1 and 7.2. The reaction mixture was passed through a column (5×70 cm) packed with 800 ml of Diaion HP-20, and eluted with water. From the water-eluted fractions, 5.25 g of sodium salt of 7β-(2D-2-amino-2-carboxy)ethylthioacetamido-7α-methoxy-3-(1-methyl-1H-tetrazol-5-yl)thiomethyl-3-cephem-4-carboxylic acid was obtained. The column of Diaion HP-20 was washed with 5% aqueous acetone to recover an additional 1.45 g of the end compound.

EXAMPLE 5

100 mg of 7β-aminoethylthioacetamido-7α-methoxycephalosporanic acid was dissolved in 10 ml of water, 61 mg of 5-mercapto-1H-tetrazole-1-ethanesulfonic acid was added to the solution, aqueous sodium bicarbonate was then added to the solution to adjust its pH to 6.8, and the mixture was heated at 60° C. for a period of 12 hours. After the reaction, the reaction mixture was treated with 1 N hydrochloric acid to bring its pH to 1.9, washed with 10 ml of ethyl acetate twice, then treated with 1 N hydrochloric acid to bring its pH to 1.0, passed through a column (2×50 cm) of Diaion HP-20, and eluted with water and 5% aqueous acetone. Fractions positive in ninhydrin reaction were combined and treated with sodium bicarbonate to adjust the pH to 7.0. The eluate was concentrated, passed through a column of Sepahdex LH-20, washed with water and eluted with 50% methanol. Fractions containing the end compound were concentrated and freeze-dried to give 50 mg of a sodium salt of 7β-aminoethylthioacetamido-7α-methoxy-3-(1-sulfoethyl-1H-tetrazol-5-yl)thiomethyl-3-cephem-4-carboxylic acid.

EXAMPLE 6

A mixture comprising 230 mg of 7β-(2D-2-amino-2-carboxy)ethylthioacetamido-7α-methoxycephalosporanic acid and 65 mg of 5-mercapto-1H-tetrazole-1-methanesulfonic acid was dissolved in 10 ml of water, and aqueous sodium bicarbonate was added to the solution to adjust its pH to 7.1, followed by reaction at 65° C. for a period of 20 hours. After the reaction, the reaction mixture was treated in the same manner as in Example 5 to give 50 mg of a sodium salt of 7β-(2D-2-amino-2-carboxy)ethylthioacetamido-7α-methoxy-3-(1-sulfomethyl-1H-tetrazol-5-yl)thiomethyl-3-cephem-4-carboxylic acid.

EXAMPLE 7

The procedure of Example 3 was repeated except that 7β-bromoacetamido-7α-methoxycephalosporanic acid (1.42 g) was dissolved in 60 ml of water and that D-cysteine was replaced by 640 mg of L-cysteine. 240 mg of a sodium salt of 7β-(2L-2-amino-2-carboxy)ethylthioacetamido-7α-methoxy-3-(1-methyl-1H-tetrazol-5-yl)thiomethyl-3-cephem-4-carboxylic acid was obtained.

EXAMPLE 8

The procedure of Example 3 was repeated except that 0.71 g of 7β-bromoacetamido-7α-methoxycephalosporanic acid was dissolved in 30 ml of water and that D-cysteine was replaced by 320 mg of D,L-cysteine. 130 mg of a sodium salt of 7β-(2D,L-2-amino-2-carboxy)ethylthioacetamido-7α-methoxy-3-(1-methyl-1H-tetrazol-5-yl)thiomethyl-3-cephem-4-carboxylic acid was obtained.

EXAMPLE 9

The sodium salt (78 mg) of 7β-(2L-2-amino-2-carboxy)ethylthioacetamido-7α-methoxy-3-(1-methyl-1H-tetrazol-5-yl)thiomethyl-3-cephem-4-carboxylic acid obtained in Example 7 was dissolved in 10 ml of water, and 50 mg of potassium cyanate was added to the solution which was then left to stand at room temperature for 2 days. After the reaction, the reaction mixture was adjusted to a pH of 6.7, passed through a column (1.5×40 cm) of Diaion HP-20 and eluted with water. Fractions containing the end compound were combined and concentrated to dryness to give 64 mg of a sodium salt of 7β-(2L-2-carbamoylamino-2-carboxy)ethylthioacetamido-7α-methoxy-3-(1-methyl-1H-tetrazol-5-yl)thiomethyl-3-cephem-4-carboxylic acid.

EXAMPLE 10

The sodium salt (200 mg) of 7β-(2D-2-amino-2-carboxy)ethylthioacetamido-7α-methoxy-3-(1-methyl-1H- tetrazol-5-yl)thiomethyl-3-cephem-4-carboxylic acid obtained in Example 4 was dissolved in 2 ml of water, the solution was treated with 1 N hydrochloric acid to adjust its pH to between 2.5 and 2.6, passed through a column packed with 100 ml of Diaion HP-20, washed with water, eluted with 20% aqueous acetone to give 184 mg of the free acid. A 140 mg of the acid was dissolved in 5 ml of water, and to this solution was added a solution of 40 mg of L-lysine in 0.8 ml of water, and the resulting mixture (pH: 7.05) was freeze-dried to give 180 mg of an L-lysine salt of 7β-(2D-2-amino-2-carboxy)ethylthioacetamido-7α-methoxy-3-(1-methyl-1H-tetrazol-5-yl)thiomethyl-3-cephem-4-carboxylic acid.

EXAMPLE 11

7β-Bromoacetamido-7α-methoxy-3-(1-methyl-1H-tetrazol-5-yl)thiomethyl-3-cephem-4-carboxylic acid (960 mg) was suspended in 20 ml of water, sodium hydrogencarbonate was added to adjust to pH of the suspension to 7.0 to form an aqueous solution of the acid. D-Homocysteine (300 mg) was added to the solution and the reaction was carried out at room temperature for a period of 1.5 hours with the pH held between 7 and 7.5. After the reaction, the reaction mixture was adjusted to a pH between 5.5 and 6.0, concentrated to a small volume, passed through a column (2×68 cm) packed with 150 ml of Diaion HP-20, and eluted with water. Fractions containing the end compound were combined, concentrated and freeze-dried to give 390 mg of sodium 7β-(3D-3-amino-3-carboxy)propylthioacetamido-7α-methoxy-3-(1-methyl-1H-tetrazol-5-yl)thiomethyl-3-cephem-4-carboxylate.

Rf in thin-layer chromatography on silica gel: 0.39 (n-butanol/acetic acid/water=2:1:1).

EXAMPLE 12

7β-Bromoacetamido-7α-methoxy-3-(p-carbamoylpyridinium)methyl-3-cephem-4-carboxylic acid (1.45 g) was dissolved in 30 ml of water, 450 mg of DL-homocysteine was added and the reaction was performed at room temperature for a period of 2 hours, with the pH of the solution held at 7.0. After the reaction, the procedure of Example 11 was repeated to give 600 mg of 7β-(3DL-3-amino-carboxy)propylthioacetamido-7α-methoxy-3-(p-carbamoylpyridinium)-methyl-3-cephem-4-carboxylic acid.

Rf in thin-layer chromatography on silica gel: 0.25 (n-butanol/acetic acid/water=2:1:1).

EXAMPLE 13

7β-Bromoacetamido-7α-methoxy-3-(1-methyl-1H-tetrazol-5-yl)thiomethyl-3-cephem-4-carboxylic acid (1.25 g) was suspended in 20 ml of water, sodium hydrogencarbonate was added to form an aqueous solution of the acid, 530 mg of D-penicillamine hydrochloride was added, and reaction was carried out at 10° C. for a period of 1.5 hours with the pH of the reaction mixture held between 7.0 and 7.5. After the reaction, the reaction mixture was treated in the same manner as in Example 11 to give 680 mg of sodium 7β-(2D-2-amino-2-carboxy-1,1-dimethyl)ethylthioacetamido-7α-methoxy-3-(1-methyl-1H-tetrazol-5-yl)thiomethyl-3-cephem-4-carboxylate was obtained.

Rf in thin-layer chromatography on silica gel: 0.45 (n-butanol/acetic acid/water=2:1:1).

EXAMPLE 14

7β-2-Bromopropionamido-7α-methoxy-3-(1-methyl-1H-tetrazol-5-yl)thiomethyl-3-cephem-4-carboxylic acid (500 mg) was suspended in 10 ml of water, sodium hydrogencarbonate was added to adjust the pH of the suspension to 7.0 to form an aqueous solution of the acid, 210 mg of D-cysteine hydrochloride was added to the solution, and the reaction was carried out at room temperature for a period of 2 hours with the pH of the reaction held between 7.0 and 7.5. After the reaction, the reaction mixture was adjusted to a pH of 6.0, concentrated to a small volume, and treated in the same manner as in Example 11 to give 230 mg of sodium 7β-[2-(2D-2-amino-2-carboxy)ethylthiopropionamido]-7α-methoxy-3-(1-methyl-1H-tetrazol-5-yl)thiomethyl-3-cephem-4-carboxylate.

Rf in thin-layer chromatography on silica gel: 0.4 (n-butanol/acetic acid/water=2:1:1).

EXAMPLE 15

7β-Bromopropionamido-7α-methoxy-3-(1-methyl-1H-tetrazol-5-yl)thiomethyl-3-cephem-4-carboxylic acid (980 mg) was suspended in 20 ml of water, sodium hydrogencarbonate was added to adjust the pH to 7.0 to thereby form an aqueous solution of the acid. 325 mg of D-cysteine was added to the solution and reaction was carried out for a period of 2 hours with the pH of the reaction mixture held between 7.0 and 7.5. The reaction mixture was treated in the same manner as in Example 11 to give 410 mg of sodium 7β-(3D-3-amino-3-carboxy)propylthiopropionamido-7α-methoxy-3-(1-methyl-1H-tetrazol-5-yl)thiomethyl-3-cephem-4-carboxylate.

Rf in thin-layer chromatography on silica gel: 0.43 (n-butanol/acetic acid/water=2:1:1).

EXAMPLE 16

Diphenylmethyl 7β-amino-7α-methoxy-3-(1-methyl-1H-tetrazol-5-yl)thiomethyl-3-cephem-4-carboxylate (1.05 g) was dissolved in 20 ml of dichloromethane, 0.35 ml of dimethylaniline was added under cooling at −20° C., then 5 ml of a solution of 1.2 g of 3D-3-t-butoxycarbonylamino-3-diphenylmethoxycarbonylpropylsulfinyl acetyl chloride in dichloromethane was added dropwise to the solution, and the reaction was carried out for a period of 3 hours. After the reaction, the reaction mixture was mixed with 100 ml of dichloromethane, washed sequentially with 5% aqueous sodium hydrogensulfate, saturated aqueous sodium chloride, and 5% aqueous sodium hydrogencarbonate, then washed with water, dehydrated with anhydrous sodium sulfate, and concentrated to dryness. The residue was dissolved in 8 ml of anisole, then 10 ml of trifluoroacetic acid was added to the solution under cooling at 0° C., and the reaction was carried out for a period of 40 minutes. After the reaction, the reaction mixture was concentrated to remove the trifluoroacetic acid. Ethyl acetate (100 ml) was added to the residue which was then extracted with 150 ml of 5% aqueous sodium hydrogencarbonate. The extract was washed with ethyl acetate and its pH was adjusted to 6.0, then it was concentrated to a small volume, and treated in the same manner as in Example 11 to give 430 mg of sodium 7β-(3D-3-amino-3-carboxy)propylsulfinylacetamido-7α-methoxy-3-(1-methyl-1H-tetrazol-5-yl)thiomethyl-3-cephem-4-carboxylate was obtained.

Rf in thin-layer chromatography on silica gel: 0.35 (n-butanol/acetic acid/water=2:1:1).

EXAMPLE 17

7β-Bromoacetamido-7α-methoxy-3-(1-methyl-1H-tetrazol-5-yl)thiomethyl-3-cephem-4-carboxylic acid (480 mg) was suspended in 15 ml of water, and sodium bicarbonate was added to the suspension to adjust its pH to 7.0 to thereby form an aqueous solution of the acid. D-Cysteine ethyl ester hydrochloride (170 mg) was added to the solution which was held at a pH of 7.0 while the reaction was continued at 5° C. for a period of 2 hours. The reaction mixture was adjusted to a pH of 6.0, passed through a column packed with 70 ml of XAD-2, washed with water, and eluted with 50% aqueous acetone. Fractions containing the end compound were concentrated and freeze-dried to give 450 mg of a white powder of 7β-(2D-2-amino-2-ethoxycarbonyl)ethylthioacetamido-7α-methoxy-3-(1-methyl-1H-tetrazol-5-yl)thiomethyl-3-cephem-4-carboxylic acid. The powder gave a single spot at an Rf of 0.6 in thin-layer chromatography on silica gel (acetone/methanol=2:1).

7β-(2D-2-amino-2-ethoxycarbonyl)ethylthioacetamido-7α-methoxy-3-(1-methyl-1H-tetrazol-5-yl)thiomethyl-3-cephem-4-carboxylic acid (310 mg) was dissolved in 5 ml of water, and the solution was treated with 1 N caustic soda at 0° C. to adjust its pH to 9.5, and was immediately freeze-dried. The freeze-dried product was suspended in 6 ml of N,N-dimethylformamide, and to the suspension, 3 ml of a solution of 220 mg of pivaloyloxymethyl iodide in N,N-dimethylformamide was added dropwise over a period of 10 minutes at −20° C., followed by a 1 hour reaction at 0° C. under stirring. The reaction mixture was diluted with 30 ml of water, washed with 30 ml of ethyl acetate at a pH of 3.0, treated with sodium bicarbonate to bring the pH to 8.0, and extracted with 100 ml of ethyl acetate. The extract was washed twice with 30 ml of water, dried with anhydrous sodium sulfate, and filtered. The filtrate was mixed with 0.3 ml of trifluoroacetic acid, and immediately concentrated to dryness to give 340 mg of a white powder of a trifluoroacetate of pivaloyloxymethyl 7β-(2D-2-amino-2-ethoxycarbonyl)ethylthioacetamido-7α-methoxy-3-(1-methyl-1H-tetrazol-5-yl)thiomethyl-3-cephem-4-carboxylate.

Rf in thin-layer chromatography on silica gel: 0.75 (ethyl acetate/acetone=5:1).

EXAMPLE 18

7β-Bromoacetamido-7α-methoxy-3-(1-methyl-1H-tetrazol-5-yl)thiomethyl-3-cephem-4-carboxylic acid (960 mg) was dissolved in 10 ml of N,N-dimethylformamide, 0.28 ml of triethylamine was added to the solution at −20° C., and to the mixture, 5 ml of a solution of 500 mg of 1-acetoxyethyl iodide in N,N-dimethylformamide was added dropwise over a period of 15 minutes, followed by a 1 hour stirring at 0° C. The reaction mixture was diluted with 50 ml of water, and extracted with 100 ml of ethyl acetate at a pH of 6.0. The extract was washed with 50 ml of water, dried with anhydrous sodium sulfate, filtered, and concentrated to dryness. The residue was washed with 30 ml of petroleum ether, and the insoluble residue was dried over phosphorus pentoxide to give 1,080 mg of a white powder of 1-acetoxyethyl 7β-bromoacetamido-7α-methoxy-3-(1-methyl-1H-tetrazol-5-yl)thiomethyl-3-cephem-4-carboxylate.

Rf in thin-layer chromatography on silica gel: 0.85 (acetone/methanol=2:1).

A 565 mg portion of the powder was dissolved in 8 ml of dioxane, 15 ml of water was added to the solution which was then treated with sodium bicarbonate to have its pH adjusted to 7.0, 180 mg of D-cysteine methyl ester hydrochloride was added to the solution, and the reaction was carried out at 0° to 5° C. for a period of 2.5 hours with the pH held between 6.5 and 6.8. The reaction mixture was diluted with 50 ml of water, extracted with 100 ml of ethyl acetate at a pH of 8.0, and then transferred to 50 ml of dilute hydrochloric acid. The extract was treated with sodium bicarbonate to have its pH adjusted to 8.0, extracted again with 100 ml of ethyl acetate, and the extract was dehydrated with anhydrous sodium sulfate, and concentrated to dryness to give 470 mg of a white powder of 1-acetoxyethyl 7β-(2D-2-amino-2-methoxycarbonyl)ethylthioacetamido-7α-methoxy-3-(1-methyl-1H-tetrazol-5-yl)thiomethyl-3-cephem-4-carboxylate.

Rf in thin-layer chromatography on silica gel: 0.70 (ethyl acetate/acetone=5:1).

EXAMPLE 19

The 1-pivaloyloxyethyl ester (620 mg) of 7β-bromoacetamido-7α-methoxy-3-(1-methyl-1H-tetrazol-5-yl)thiomethyl-3-cephem-4-carboxylic acid obtained by the method of Example 18 was dissolved in 10 ml of tetrahydrofuran, 20 ml of water was added to the solution which was then treated with aqueous sodium bicarbonate to have its pH adjusted to 7.0, 190 mg of D-cysteine hydrochloride was added to the solution, and the reaction was carried out at 0° to 5° C. for a period of 2 hours with the pH held between 6.5 and 6.8. The reaction mixture was adjusted to a pH of 5.5, immediately freeze-dried, and the residue was extracted with 20 ml of acetone. The solvent was evaporated to dryness, and the resulting solid was dissolved in 50 ml of water, and washed with 50 ml of ethyl acetate at a pH of 2.0. The aqueous layer was again adjusted to a pH of 5.5, saturated with sodium chloride, and extracted with 100 ml of ethyl acetate three times. The extracts were combined and dried with anhydrous sodium sulfite, and concentrated to dryness to give 380 mg of a white powder of 1-pivaloyloxyethyl 7β-(2D-2-amino-2-carboxy)ethylthioacetamido-7α-methoxy-3-(1-methyl-1H-tetrazol-5-yl)thiomethyl-3-cephem-4-carboxylate.

Rf in thin-layer chromatography on silica gel: 0.2 (acetone/methanol=2:1).

EXAMPLE 20

7β-(2D-2-t-Butoxycarbonylamino-2-carboxy)ethylthioacetamido-7α-methoxy-3-(1-methyl-1H-tetrazol-5-yl)thiomethyl-3-cephem-4-carboxylic acid (1.25 g) was dissolved in 20 ml of N,N-dimethylformamide, 0.66 ml of triethylamine was added to the solution under cooling at −15° C., and to the mixture a solution of 1.2 g of pivaloyloxymethyl iodide in N,N-dimethylformamide was added dropwise over a period of 20 minutes, followed by a 1 hour reaction under stirring. The reaction mixture was poured into 100 ml of ice water, and extracted with 100 ml of ethyl acetate twice. The extracts were combined, washed with 50 ml of water three times, dehydrated with anhydrous sodium sulfate, and concentrated to dryness. The residue was washed with 20 ml of petroleum ether to give 1.02 g of a pale yellow syrup of pivaloyloxymethyl 7β-(2D-2-t-butoxycarbonylamino-2-pivaloyloxymethoxycarbonyl)ethylthioacetamido-7α-methoxy-3-(1-methyl-1H-tetrazol-5-yl)thiomethyl-3-cephem-4-carboxylate.

A 450 mg portion of the syrup was dissolved in 4 ml of trifluoroacetic acid at −10° C. and left to stand for 20 minutes. The trifluoroacetic acid was removed by evaporation, the reaction mixture which was then passed through a column packed with 100 ml of Sephadex LH-20 and eluted with acetone. Fractions containing the end compound were combined and concentrated to dryness to thereby give 260 mg of a white powder of pivaloyloxymethyl 7β-(2D-2-amino-2-pivaloyloxymethoxycarbonyl)ethylthioacetamido-7α-methoxy-3-(1-methyl-1H-tetrazol-5-yl)thiomethyl-3-cephem-4-carboxylate.

Rf in thin-layer chromatography on silica gel: 0.33 (ethyl acetate/acetone=5:1).

EXAMPLE 21

7β-(3D,L-3-amino-3-carboxy)propylthioacetamido-7α-methoxy-3-(1-methyl-1H-tetrazol-5-yl)thiomethyl-3-cephem-4-carboxylic acid (250 mg) was dissolved in a mixture of 4.0 ml of N,N-dimethylformamide and 1.5 ml of dichloromethane, and 0.135 ml of triethylamine was added to the resulting solution. Then, 3 ml of a dichloromethane solution containing 80 μl of methoxymethyl chloride was added dropwise at −35° C. over a period of 30 minutes, followed by a 3-hour reaction at −35° C. under stirring. The reaction mixture was poured into 50 ml of ice water, and extracted three times with 50 ml of ethyl acetate at a pH of 8.0. The extracts were combined, washed with water, dehydrated with anhydrous sodium sulfate, and concentrated to dryness. The residue was washed with 10 ml of hexane, dissolved in 3 ml of dioxane and freeze-dried to give 80 mg of a white powder of methoxymethyl 7β-(3D,L-3-amino-3-methoxymethoxycarbonyl)propylthoacetamido-7α-methoxy-3-(1-methyl-1H-tetrazol-5-yl)thiomethyl-3-cephem-4-carboxylate.

Rf in thin-layer chromatography on silica gel: 0.19 (ethyl acetate/acetone=5:1).

While the invention has been described in detail and with reference to specific embodiments thereof, it will be apparent to one skilled in the art that various changes and modifications can be made therein without departing from the spirit and scope thereof.

What is claimed is:

1. A 7α-methoxycephalosporin derivative of the formula (I-a):

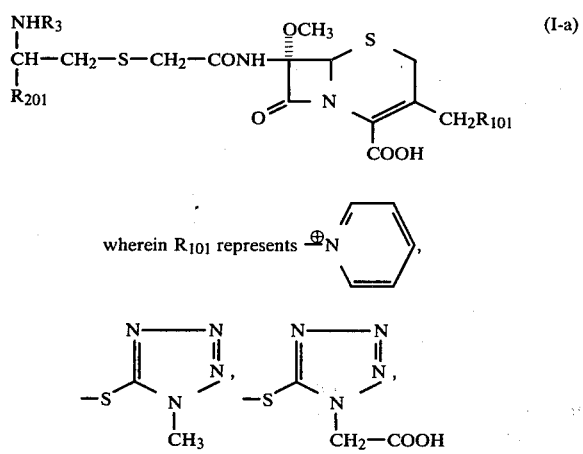

$R_{201}$ represents a hydrogen atom or a carboxy group; $R_3$ represents a hydrogen atom, a carbamoyl group or a lower acyl group; or a pharmaceutically acceptable salt thereof.

2. The 7α-methoxycephalosporin derivative according to claim 1, wherein the acyl group of $R_3$ is a formyl group, an acetyl group, a trifluoroacetyl group, a propionyl group, a glycyl group or an alanyl group, and a pharmaceutically acceptable salt thereof.

3. The 7α-methoxycephalosporin derivative according to claim 1, which is represented by the formula:

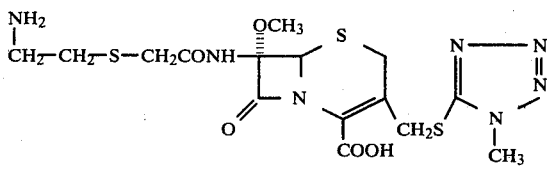

and a pharmaceutically acceptable salt thereof.

4. The 7α-methoxycephalosporin derivative according to claim 1, which is represented by the formula:

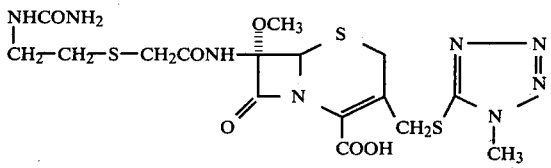

and a pharmaceutically acceptable salt thereof.

5. The 7α-methoxycephalosporin derivative according to claim 1, which is represented by the formula:

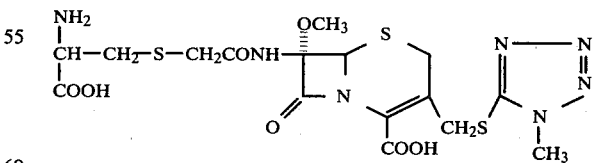

and a pharmaceutically acceptable salt thereof.

6. A pharmaceutical composition having antibacterial activity comprising a 7α-methoxycephalosporin derivative of claim 1 as an active ingredient and a carrier or diluent.

7. The 7α-methoxycephalosporin derivative according to claim 1, wherein $R_{201}$ represents a carboxy group.

* * * * *